(12) United States Patent
Yuan et al.

(10) Patent No.: US 12,691,141 B2
(45) Date of Patent: Jul. 28, 2026

(54) USE OF MICRO- AND NANO-MgH2 COMPOUND PARTICLES IN INHIBITION OF LEISHMANIA INFECTION AND TREATMENT OF LEISHMANIASIS

(71) Applicant: SHANGHAI JIAO TONG UNIVERSITY, Shanghai (CN)

(72) Inventors: Guangyin Yuan, Shanghai (CN); Monica Echeverry Rendon, Shanghai (CN); Liang Jin, Shanghai (CN); Sara Maria Robledo Restrepo, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 725 days.

(21) Appl. No.: 17/924,336

(22) PCT Filed: Feb. 4, 2021

(86) PCT No.: PCT/CN2021/075141
§ 371 (c)(1),
(2) Date: Nov. 9, 2022

(87) PCT Pub. No.: WO2021/227572
PCT Pub. Date: Nov. 18, 2021

(65) Prior Publication Data
US 2023/0181626 A1    Jun. 15, 2023

(30) Foreign Application Priority Data
May 9, 2020    (CN) ......................... 202010387358.X

(51) Int. Cl.
*A61K 33/06*        (2006.01)
*A61K 9/51*         (2006.01)
(Continued)

(52) U.S. Cl.
CPC ................ *A61K 33/06* (2013.01); *A61K 9/51* (2013.01); *A61P 33/02* (2018.01); *B82Y 5/00* (2013.01); *B82Y 30/00* (2013.01)

(58) Field of Classification Search
CPC ....................................................... B82Y 5/00
See application file for complete search history.

(56) References Cited

FOREIGN PATENT DOCUMENTS

CN        101951929 A        1/2011
CN        102908361 A        2/2013
(Continued)

OTHER PUBLICATIONS

Ali Jebali et al., Lectin coated MgO nanoparticle: its toxicity, antileishmanial activity, and macrophage activation, Drug and Chemical Toxicology, Jan. 2014 (Year: 2014).*
(Continued)

*Primary Examiner* — Sharmila G Landau
(74) *Attorney, Agent, or Firm* — Bayramoglu Law Offices LLC

(57) ABSTRACT

A use of micro- and nano-MgH$_2$ compound particles in the inhibition of *Leishmania* infection and in the treatment of Leishmaniasis is provided. The micro- and nano-MgH$_2$ compound particles can be used to prepare a pharmaceutical composition for inhibiting *Leishmania* or to prepare a pharmaceutical composition for treating a skin or mucosal ulcer or visceral damage caused by *Leishmania* infection. The present disclosure discovers for the first time that the micro- and nano-MgH$_2$ compound particles can significantly reduce the number of *Leishmania* in macrophages and inhibit the proliferation of *Leishmania*, indicating a very prominent insecticidal inhibition effect. The micro- and nano-MgH$_2$ compound particles of the present disclosure can quickly and effectively cure a skin ulcer and/or a mucosal ulcer caused by *Leishmania* and an impaired function of an
(Continued)

internal organ (mainly liver and spleen) caused by *Leishmania* and have high biosafety and huge clinical application values.

3 Claims, 4 Drawing Sheets

(51) Int. Cl.

| | | |
|---|---|---|
| *A61P 33/02* | (2006.01) | |
| *B82Y 5/00* | (2011.01) | |
| *B82Y 30/00* | (2011.01) | |

(56) References Cited

FOREIGN PATENT DOCUMENTS

| | | | | |
|---|---|---|---|---|
| CN | 103415294 A | 11/2013 | | |
| CN | 105456288 A | 4/2016 | | |
| CN | 109453167 A | 3/2019 | | |
| CN | 110559467 A | 12/2019 | | |
| WO | WO2017101887 A1 * | 6/2017 | ............. | A61K 33/06 |

OTHER PUBLICATIONS

WO2017101887a1, Google English Translation document, downloaded in Mar. 2025 (Year: 2025).*

Ali Fatahi Bafghi, et al., Magnesium oxide nanoparticles coated with glucose can silence important genes of Leishmania major at sub-toxic concentrations, Colloids and Surfaces B: Biointerfaces, 2015, pp. 300-304, vol. 136.

Ali Jebali, et al., Nano-based antileishmanial agents: A toxicological study on nanoparticles for future treatment of cutaneous leishmaniasis, Toxicology in Vitro, 2013, pp. 1896-1904, vol. 27.

Shen Zhenzhong, Preparation of New Maleimide Structure-Containing Antibacterial Agent and Research on its Antifungal Activity, Master's thesis of Zhejiang University of Technology, 2012, pp. 16.

Retrieved from: https://www.who.int/leishmaniasis/en/, Leishmaniasis, World Health Organization.

Esther Guerrero, et al., Role of Positional Hydrophobicity in the Leishmanicidal Activity of Magainin 2, Antimicrobial Agents and Chemotherapy, 2004, pp. 2980-2986, vol. 48, No. 8.

Henrique Lanza, et al., Comparative effect of ion calcium and magnesium in the activation and infection of the murine macrophage by Leishmania major, Biol Res, 2004, pp. 385-393, vol. 37.

Davidson RN, Advances in the treatment of visceral leishmaniasis, Medicine Abroad (Parasitic Diseases fascicle), 1994, pp. 27-29.

B. M. Buchholz, et al., Hydrogen Inhalation Ameliorates Oxidative Stress in Transplantation Induced Intestinal Graft Injury, American Journal of Transplantation, 2008, pp. 2015-2024, vol. 8.

Hong-Guang Chen, et al., Heme oxygenase-1 mediates the anti-inflammatory effect of molecular hydrogen in LPS-stimulated RAW 264.7 macrophages, International Journal of Surgery, 2013, pp. 1060-1066, vol. 11.

* cited by examiner

USE OF MICRO- AND NANO-MgH2 COMPOUND PARTICLES IN INHIBITION OF LEISHMANIA INFECTION AND TREATMENT OF LEISHMANIASIS

CROSS REFERENCE TO THE RELATED APPLICATIONS

This application is the national phase entry of International Application No. PCT/CN2021/075141, filed on Feb. 4, 2021, which is based upon and claims priority to Chinese Patent Application No. 202010387358.X, filed on May 9, 2020, the entire contents of which are incorporated herein by reference.

TECHNICAL FIELD

The present disclosure belongs to the technical field of medicine and specifically relates to the use of micro- and nano-MgH$_2$ compound particles in the inhibition of *Leishmania* infection and in the treatment of Leishmaniasis. In particular, the present disclosure relates to the use of micro- and nano-MgH$_2$ compound particles in the inhibition of mucocutaneous Leishmaniasis (MCL) and in the treatment of a skin ulcer and/or a mucosal ulcer caused by *Leishmania* infection and an impaired function of an internal organ (spleen, liver, bone marrow, or the like) caused by visceral Leishmaniasis (VL).

BACKGROUND

Leishmaniasis is an epidemic disease in the tropics. Leishmaniasis is mainly an intracellular parasite (*Leishmania*) disease caused by the spread of sandflies. Leishmaniasis can appear anywhere in the world and is prevalent in tropical and subtropical regions. 98 countries are affected by Leishmaniasis, and more than 15 million people in Asia, Africa, Southern Europe, and Central and South America suffer from Leishmaniasis. Leishmaniasis cases in China are mainly distributed in Xinjiang, Inner Mongolia, Gansu, Sichuan, Shaanxi, and Shanxi provinces. 70,000 or more deaths are caused by Leishmaniasis worldwide every year, and *Leishmania* is a conditionally pathogenic parasite in AIDS patients. (reference: https://www.who.int/leishmaniasis/en/).

Leishmaniasis is mainly manifested as Leishmaniadonovani and Leishmaniabraziliensis, and MCL has the highest incidence. VL is caused by *Leishmania* invasion of internal organs (spleen, liver, bone marrow, and the like) and often causes death if not treated timely. MCL is mainly caused by the parasitism of *Leishmania braziliensis* in the skin, and *Leishmania braziliensis* can also invade the nasopharynx or ear mucosa through lymph or blood, resulting in mucosal lesions. MCL is clinically manifested as local lesions of the skin throughout the body after infection. The skin lesions are characterized by mostly skin nodules and, in some cases, a few areas of fading skin color. The nodules are granulomas of varying sizes or dark papules and can be rarely cured without rupturing. The nodules can be connected into patches similar to neoplastic leprosy, and *Leishmania* without *flagellates* can be observed in the nodules. Skin lesions are common on the face and neck, and the course of the disease can last for decades or even a lifetime, severely reducing the quality of life of a patient.

A pathological mechanism of the disease is as follows: *Leishmania* infects the human body with the participation of an intermediate host, swims in a tissue, and is eventually engulfed by macrophages specifically, and *Leishmania* survives and multiplies in the cytoplasmic phagolysosome, thereby becoming an intracellular parasite of macrophage-specific infection. Cutaneous pathology is mainly manifested as a large amount of infected macrophage infiltration that leads to a local chronic inflammatory response, and corresponding skin tissue cannot be cured in a short time, resulting in a skin lesion.

At present, Leishmaniasis is clinically treated with a 5-valent antimony preparation, specifically sodium antimony gluconate, which has a strong insecticidal effect on *Leishmania* but leads to obvious side effects, such as continuous reduction of leukocytes especially neutrophil granulocytes during treatment. In addition, patients with heart, liver, and kidney diseases show poor tolerance to the antimony preparation. Some patients cannot be cured after three courses of antimony treatment and are called anti-antimony patients. In addition, the systemic treatment for cutaneous Leishmaniasis has low therapeutic activity, large side effects, and high costs.

Although considerable progress has been made in the field of parasite-related biochemistry and biology, it is currently urgent to develop a new method for treating the disease due to the high treatment cost, long duration, and serious side effects. Unfortunately, Leishmaniasis often occurs in poor areas, and there is no economic incentive for researching Leishmaniasis in the pharmaceutical industry. Thus, Leishmaniasis is easily overlooked. Healthcare institutions in the affected countries are focusing on finding alternatives to reduce the toxicity, cost, and treatment time of the current treatment with an antimony-containing drug.

According to search results, the Chinese Patent CN109453167A discloses the use of a maleimide compound in the preparation of a *Leishmania* insecticide, and the maleimide compound has an anti-*Leishmania* activity higher than existing drugs. However, maleimide compounds are of single species and are not easy to separate, and some maleimide compounds have a high toxicity. In addition, the antibacterial activity of maleimide compounds is highly dependent on the pH value, and thus the maleimide compounds are a group of passive antibacterial materials relying on an acidic environment (reference: Shen Zhenzhong, Preparation of New Maleimide Structure-Containing Antibacterial Agent and Research on its Antifungal Activity, Master's thesis of Zhejiang University of Technology (ZJUT), May 2012, P.16). In this patent document, only the in vitro cell experiment and prospect effect prediction are conducted, and an actual therapeutic effect in animals is not illustrated. It can be seen that how to effectively treat or alleviate cutaneous Leishmaniasis has become an urgent issue. There is currently a need to develop a durable, stable, and side-effect-free effective therapeutic drug for treating a skin lesion and internal organ damage due to skin tissue unable to be cured in a short time caused by Leishmaniasis.

SUMMARY

An objective of the present disclosure is to overcome the shortcomings of the prior art and provide the use of micro- and nano-MgH$_2$ compound particles in the inhibition of *Leishmania* infection and in the treatment of Leishmaniasis, and particularly use of micro- and nano-MgH$_2$ compound particles in the inhibition of *Leishmania* and in the treatment of skin and mucosal ulcers caused by *Leishmania* infection and internal organ damage caused by *Leishmania* infection.

The objective of the present disclosure is achieved by the following technical solutions.

In a first aspect, the present disclosure provides a use of MgH$_2$ in the preparation of a pharmaceutical composition for inhibiting *Leishmania*.

In a second aspect, the present disclosure provides a use of MgH$_2$ in the preparation of a pharmaceutical composition for treating a skin or mucosal ulcer caused by *Leishmania* infection.

In a third aspect, the present disclosure provides a use of MgH$_2$ in the preparation of a pharmaceutical composition for treating visceral damage caused by *Leishmania* infection.

Preferably, the micro- and nano-MgH$_2$ compound particles each have a particle diameter of 1 nm to 10 μm.

Preferably, the micro- and nano-MgH$_2$ compound particles each have a particle diameter of 100 nm to 1,000 nm.

Preferably, in the pharmaceutical composition, an effective concentration of MgH$_2$ is 1 to 15 mg/100 μL.

In a fourth aspect, the present disclosure provides a pharmaceutical composition for inhibiting *Leishmania*, including: micro- and nano-MgH$_2$ compound particles and a pharmaceutically acceptable carrier and/or adjuvant.

In a fifth aspect, the present disclosure provides a pharmaceutical composition for treating a skin or mucosal ulcer caused by *Leishmania* infection, including: micro- and nano-MgH$_2$ compound particles and a pharmaceutically acceptable carrier and/or adjuvant.

In a sixth aspect, the present disclosure provides a pharmaceutical composition for treating visceral damage caused by *Leishmania* infection, including: micro- and nano-MgH$_2$ compound particles and a pharmaceutically acceptable carrier and/or adjuvant.

Preferably, the micro- and nano-MgH$_2$ compound particles each have a particle diameter of 1 nm to 10 μm.

Preferably, the micro- and nano-MgH$_2$ compound particles each have a particle diameter of 100 nm to 1,000 nm.

A pharmacological action of the present disclosure is as follows:

1. The micro- and nano-MgH$_2$ compound particles of the present disclosure can produce a large number of reactive oxygen species (ROS) (such as hydroxyl radicals and superoxide anions) through hydrolysis, and the ROS can effectively kill *Leishmania*.
2. The micro- and nano-MgH$_2$ compound particles of the present disclosure may be hydrolyzed into hydrogen and magnesium hydroxide in the cytoplasm, thereby changing an intracellular microenvironment. The magnesium hydroxide can rapidly alkalize the cytosolic environment and change an acidic environment conducive to the growth of *Leishmania* in phagolysosomes, thereby inhibiting the growth of *Leishmania*.
3. The magnesium ions and hydrogen molecules in the degradation products of the micro- and nano-MgH$_2$ compound particles can cause anti-inflammatory responses to inhibit the expression of inflammatory factors in macrophages and promote inflammation digestion at a skin lesion. In addition, the magnesium ions can also promote the growth of endothelial cells, enrich the capillaries at a skin lesion, and promote the repair of skin tissue. Thus, the effect of treating a skin ulcer and/or a mucosal ulcer caused by *Leishmania* can be achieved.

An administration mode of the present disclosure may be as follows: The MgH$_2$ particles or a composition thereof is first dispersed in a glycerol or PBS solution to obtain a solution with a MgH$_2$ particle concentration of 1-15 mg/100 μL. The solution is smeared or sprayed onto the skin and mucosal ulceration 1 to 3 times every day, and the wound will heal within 1 to 2 weeks. A capsule including the micro- and nano-MgH$_2$ compound particles can also be administered orally to act on a damaged internal organ (mainly liver, spleen, or the like).

Compared with the prior art, the present disclosure has the following beneficial effects.

1. The present disclosure discovers for the first time that the micro- and nano-MgH$_2$ compound particles can significantly reduce the number of *Leishmania* in macrophages and inhibit the proliferation of *Leishmania*, indicating a very prominent insecticidal inhibition effect.
2. The micro- and nano-MgH$_2$ compound particles of the present disclosure can quickly and effectively cure a skin ulcer and/or a mucosal ulcer caused by *Leishmania* and an impaired function of an internal organ (mainly liver and spleen) caused by *Leishmania*. Experimental results of the present disclosure show that the 5-valent antimony preparation (sodium antimony gluconate) requires a cure time of 1 to 3 months, and the present disclosure shortens the cure time to 2 to 4 weeks.
3. It has been confirmed by experiments that the micro- and nano-MgH$_2$ compound particles used in the present disclosure have high biosafety and can be directly smeared to skin and mucosal ulcers for treatment or can be orally administered in the form of a capsule to act on a damaged internal organ. However, the 5-valent antimony preparation (sodium antimony gluconate) has obvious side effects and needs to be injected for treatment, resulting in low patient compliance. Therefore, the micro- and nano-MgH$_2$ compound particles have huge clinical application values.

BRIEF DESCRIPTION OF THE DRAWINGS

FIG. 1A shows the hydrogen content; FIG. 1B shows the magnesium ion concentration; and FIG. 1C shows the pH value.

FIG. 5A shows the body weight change; FIG. 5B shows the spleen weight; and FIG. 5C shows the liver and kidney function indexes.

DETAILED DESCRIPTION OF THE EMBODIMENTS

The present disclosure is described in detail below with reference to specific examples. The following examples will help those skilled in the art to further understand the present disclosure but do not limit the present disclosure in any way. It should be noted that those of ordinary skill in the art can further make several variations and improvements without departing from the idea of the present disclosure. These all fall within the protection scope of the present disclosure.

Example 1

Figure 1A:
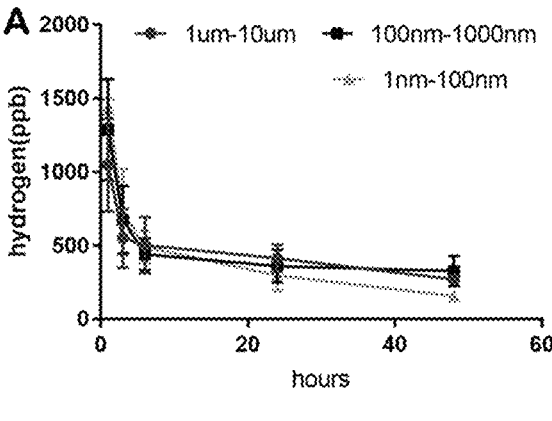
FIGS. 1A-1C show the influence of three types of micro- and nano-MgH$_2$ compound particles on the hydrogen content, magnesium ion concentration, and pH value of a cell culture medium (RPMI1640), where
Figure 1B:
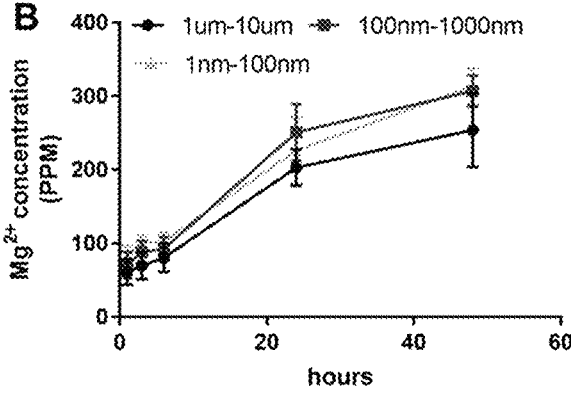
Figure 1C:
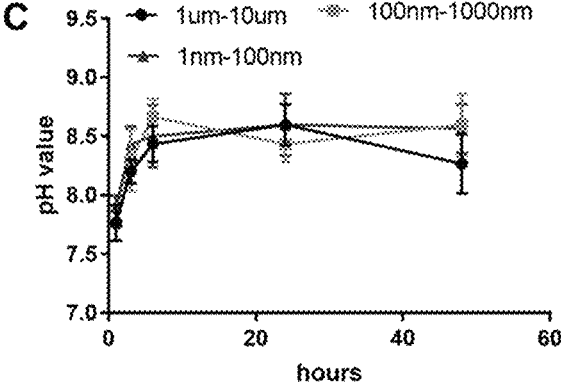

MgH$_2$ compound particles of different particle sizes were continuously monitored for hydrogen release, magnesium ion concentration, and pH. A specific process was as follows:

Three types of MgH$_2$ particles respectively with particle diameters of 1 nm to 100 nm, 100 nm to 1,000 nm, and 1 μm to 10 μm each were added dropwise to a cell culture dish at a final concentration of 1 mg/mL and incubated for 48 h, and the hydrogen release, magnesium ion concentration, and pH were continuously monitored. Monitoring results were shown in FIGS. 1A-1C. It can be seen from the results that the three types of MgH$_2$ particles with different particle diameters can produce high-concentration hydrogen in an initial stage, and the hydrogen concentration continues to decrease over time, and the magnesium ion concentration continues to increase, and the pH value continues to rise and is gradually stabilized at about 8.5.

24 H: 0.261 mg/mL

48 H: 0.290 mg/mL

72 H: 0.306 mg/mL

2) The influence of micro- and nano-MgH$_2$ compound particles on THP-1-derived macrophages infected by *Leishmania* (Leishmaniadonovani) was tested.

The optimal infection number and infection time were determined. Different *Leishmania* proliferation stages (5 d or 6 d), infection proportions (5 to 30 protozoa/cell), and infection times (3 h or 24 h) were set, and the number of infected cells was counted by Giemsa staining to determine the highest infection efficiency group and the lowest infection efficiency group. Results showed that the experimental group with 5 d *Leishmania*, 5 protozoa/cell, and 3 h infection had the lowest infection efficiency while the experimental group with 5 d *Leishmania*, 15 protozoa/cell, and 24 h infection had the highest infection efficiency (Table 1 and FIG. 3). Thus, the above two experimental groups were selected for follow-up investigation.

TABLE 1

Infection results of co-cultivation of *Leishmaniadonovani* and macrophages in different ratios

| | Infection for 3 h | | Infection for 24 h | |
|---|---|---|---|---|
| | Number of infected cells | Total number of parasites | Number of infected cells | Total number of parasites |
| 5 d *Leishmania* | | | | |
| 5 parasites/cell | 145 | 535 | 85 | 505 |
| 10 parasites/cell | 26 | 1245 | 415 | 3545 |
| 15 parasites/cell | 175 | 565 | 33 | 3565 |
| 20 parasites/cell | 20 | 775 | 28 | 1975 |
| 30 parasites/cell | 34 | 3755 | 45 | 5995 |
| 6 d *Leishmania* | | | | |
| 5 parasites/cell | 185 | 67 | 22 | 2355 |
| 10 parasites/cell | 21 | 855 | 28 | 242 |
| 15 parasites/cell | 225 | 130 | 31 | 537 |
| 20 parasites/cell | 255 | 1145 | 325 | 461 |
| 30 parasites/cell | 355 | 3085 | 40 | 521 |

Note:
The number of infected cells and the number of parasites are expressed in a consistent unit.

Example 2

Figures 2, 3:
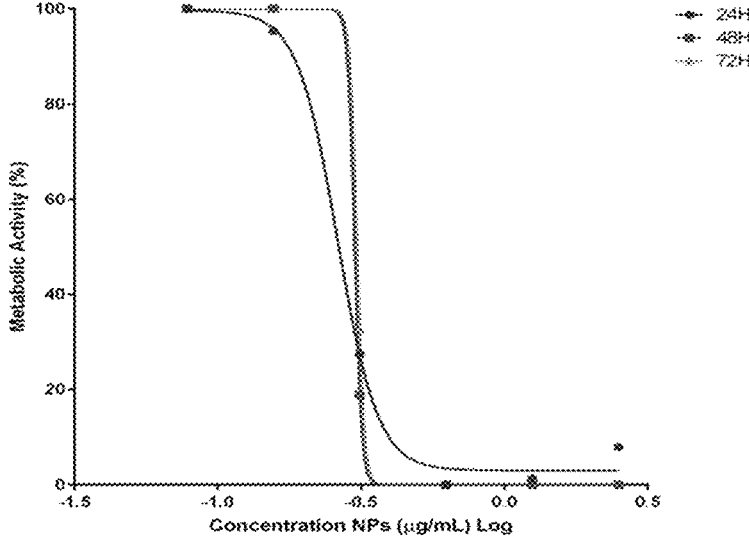
FIG. 2 shows the IC$_{50}$ effect of micro- and nano-MgH$_2$ compound particles on macrophages.
FIG. 3 is an image of Leishmaniadonovani-infected macrophages.
Figure 4:
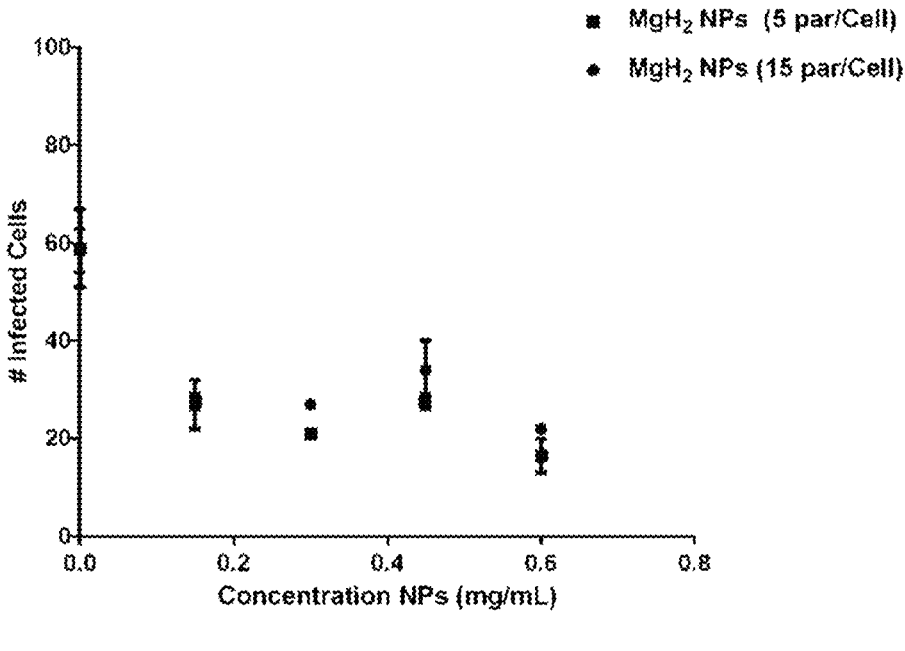
FIG. 4 shows the relationship between micro- and nano-MgH$_2$ compound particle concentrations and *Leishmania* (Leishmaniadonovani)-infected cells.

Micro- and nano-MgH$_2$ compound particles were co-cultivated with *Leishmania* (Leishmaniadonovani)-infected macrophages as follows:

1) The IC$_{50}$ (half inhibition concentration, that is, a concentration at which half of the cell activity was inhibited) of MgH$_2$ compound particles on macrophages was first determined. Magnesium hydride particles (100 nm to 1,000 nm) were co-cultivated with THP-1-derived macrophages for 72 h, and the cytotoxicity was tested by CCK-8 (FIG. 2). It was found that IC50 values at different cultivation time points were different:

Subsequently, micro- and nano-MgH$_2$ compound particles (100 nm to 1,000 nm) were co-cultivated with infected macrophages (medium RPMI1640) for 48 h. The number of infected cells and the number of protozoa were observed through Giemsa staining. As shown in FIG. 4 and Table 2, with the increase of magnesium hydride concentration, the number of infected cells and the number of protozoa decreased in a concentration-dependent manner, and it was calculated that EC50=0.043 mg/mL (EC50 was a half effect concentration, namely, a dose causing 50% of subjects to produce a specific effect), which was significantly lower than IC50=0.290 mg/mL. It indicates that the micro- and nano-MgH$_2$ compound particles can significantly inhibit the infection of macrophages without compromising biosafety.

TABLE 2

Therapeutic effects of micro- and nano-MgH$_2$ compound particles at different concentrations on macrophages infected by *Leishmaniadonovani*

| mg/mL | 24 H | | 48 H | | 72 H | |
|---|---|---|---|---|---|---|
| | Number of infected cells | Number of parasites | Number of infected cells | Number of parasites | Number of infected cells | Number of parasites |
| 15-parasite group | | | | | | |
| 0.6 | 22 | 66 | 7 | 15 | ND | ND |
| 0.45 | 34 | 91 | 14 | 23 | ND | ND |
| 0.3 | 27 | 119 | 24 | 85 | 61 | 254 |
| 0.15 | 27 | 88 | 23 | 65 | 60 | 281 |
| Control group | 59 | 195 | 79 | 196 | 71 | 608 |
| 5-parasite group | | | | | | |
| 0.6 | 17 | 55 | ND | ND | ND | ND |
| 0.45 | 28 | 59 | 13 | 31 | ND | ND |
| 0.3 | 21 | 55 | 24 | 64 | 50 | 162 |
| 0.15 | 28 | 117 | 26 | 60 | 53 | 214 |
| Control group | 59 | 333 | 55 | 120 | 81 | 705 |

Notes:

In the control group, a pure cell culture medium is added instead of the micro- and nano-MgH$_2$ compound particles. The number of infected cells and the number of parasites are expressed in a consistent unit.

Example 3 Verification by Animal Experiments

Figure 5A:
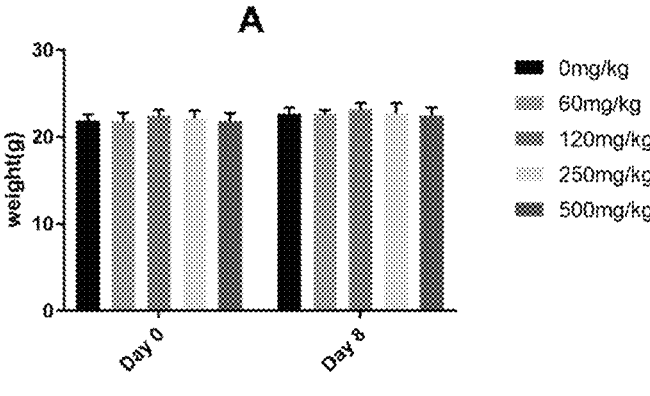
FIGS. 5A-5C show the assessment results of in vivo biosafety of micro- and nano-MgH$_2$ compound particles, where
Figure 5B:
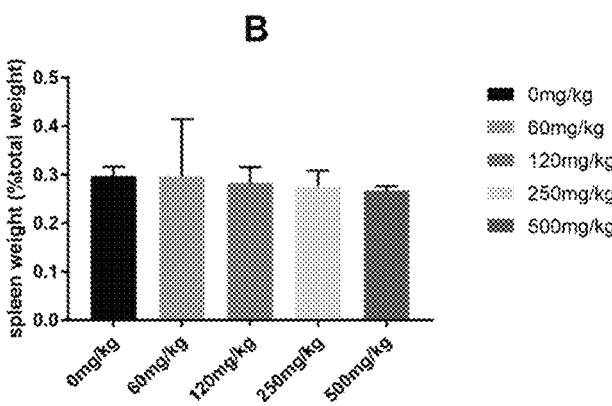
Figure 5C:
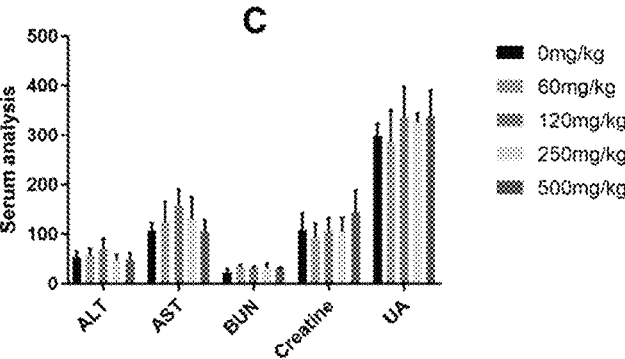

1) Biosafety verification: C57BL/6 mice were selected and intragastrically administered with micro- and nano-MgH$_2$ compound particles (100 nm to 1,000 nm) at different concentrations (0 mg/kg, 60 mg/kg, 120 mg/kg, 250 mg/kg, and 500 mg/kg) every day, and various physiological indexes were observed on day 8. As shown in FIGS. 5A-5C, the survival rate of mice was 100%, and the body weight, spleen weight, and liver and kidney indexes were normal.

2) Research on the treatment with micro- and nano-MgH$_2$ compound particles:

2.1 MgH$_2$ compound particles with a particle diameter of 100 nm to 1,000 nm were first dissolved in a phosphoric acid buffer to prepare 5 concentration groups (1 mg/100 uL, 3 mg/100 uL, 5 mg/100 uL, 10 mg/100 uL, and 15 mg/100 uL).

2.2 A Leishmaniabraziliensis-infected mouse model was established, which was specified as follows:

Various hamsters (Mesocricetus auratus) were selected, the lower dorsal margin was shaved, and *Leishmania* (1 million/100 uL/mouse) was injected subcutaneously at 2 cm of an upper margin of a tail. A skin change at an injection site was observed every day, and after the hamsters were raised for 4 to 8 weeks, it was observed that a skin tissue at the injection site was bright red, tended to bleed, and underwent fresh granulation tissue hyperplasia and hair loss that could not be cured in a short time, indicating that a skin ulcer was formed and the model was successfully established.

2.3 35 hamster models infected by *Leishmania* were divided into 7 groups, with 5 hamster models per group. MgH$_2$ compound particles (with a particle size of 100 nm to 1,000 nm) at different concentrations (100 uL) were smeared to a skin lesion of an infected hamster once every 24 h continuously for 14 d. An untreated group (namely, a blank control group, infected mice were not treated) and an antimony preparation subcutaneous injection group (sodium antimony gluconate (5-valent antimony preparation, 200 µg/mL) was injected subcutaneously at an ulcer site 100 µL/mouse/d) were set. After treatment in each experimental group, a healing rate of a skin ulceration wound was shown in Table 3 below.

TABLE 3

Efficacy of micro- and nano-MgH$_2$ compound particles at different doses on skin ulceration of *Leishmania*-infected hamsters

| MgH$_2$ particle diameter | Concentration | Healing rate of a skin ulceration wound, %/day 0 | Healing rate of a skin ulceration wound, %/day 3 | Healing rate of a skin ulceration wound, %/day 7 | Healing rate of a skin ulceration wound, %/day 14 |
|---|---|---|---|---|---|
| 100 nm-1000 nm | 1 mg/100 ul | 0 | 3.3 ± 2.1 | 18.4 ± 3.2 | 42.5 ± 6.5 |
| | 3 mg/100 ul | 0 | 5.2 ± 1.5 | 38.7 ± 5.5 | 71.3 ± 6.1 |
| | 5 mg/100 ul | 0 | 7.4 ± 1.8 | 53.5 ± 4.4 | 91.2 ± 5.4 |
| | 10 mg/100 ul | 0 | 13.1 ± 2.3 | 75.3 ± 4.6 | 100 |
| | 15 mg/100 ul | 0 | 14.4 ± 2.5 | 80.2 ± 4.9 | 100 |
| Untreated group | | 0 | 0 | 0 | 0 |
| Antimony preparation subcutaneous injection group | | 0 | 15.3 ± 2.0 | 75.2 ± 4.8 | 88.9 ± 5.1 |

The above-mentioned animal studies have shown that, compared with the untreated group, the MgH$_2$ compound particle treatment group can improve the clinical symptoms of a skin lesion in a concentration-dependent manner, inhibit the number of *Leishmania* in macrophages, reduce the infiltration of inflammatory cells and inflammatory factors at a skin lesion, significantly enhance the tissue repair, significantly reduce the area of a skin lesion, make hair follicles grow vigorously, and accelerate the healing of a wound in a skin lesion area. In addition, studies have shown that, in the magnesium hydride particle oral administration group, there is no significant damage to the liver and kidney functions of mice (FIG. 5C), the body weight (FIG. 5A), spleen (FIG. 5B), cardiopulmonary and brain tissues, and blood routine are normal, and there is no organ and tissue damage. Existing studies have shown that the antimony preparation can cause serious liver and kidney function damage and even cause side effects such as death.

There are many ways to specifically apply the present disclosure, and the above are merely preferred implementations of the present disclosure. It should be noted that the above examples are provided only for illustrating the present disclosure and are not intended to limit the protection scope of the present disclosure. For a person of ordinary skill in the art, several improvements may further be made without departing from the principle of the present disclosure, and such improvements should also be considered as falling within the protection scope of the present disclosure.

What is claimed is:

1. A method of inhibiting *Leishmania* comprising a step of administering a pharmaceutical composition to a subject in need thereof, wherein the pharmaceutical composition comprises micro- and nano-$MgH_2$ compound particles and a pharmaceutically acceptable carrier and/or adjuvant; and an effective concentration of $MgH_2$ is 1 mg/100 uL to 15 mg/100 uL, wherein the micro- and nano-$MgH_2$ compound particles each have the particle diameter of 100 nm to 1,000 nm.

2. A method of treating a skin or mucosal ulcer caused by a *Leishmania* infection comprising a step of administering a pharmaceutical composition to a subject in need thereof, wherein the pharmaceutical composition comprises micro- and nano-$MgH_2$ compound particles and a pharmaceutically acceptable carrier and/or adjuvant and an effective concentration of $MgH_2$ is 1 mg/100 uL to 15 mg/100 L wherein the micro- and nano-$MgH_2$ compound particles each have the particle diameter of 100 nm to 1,000 nm.

3. A method of treating a visceral damage caused by a *Leishmania* infection comprising a step of administering a pharmaceutical composition to a subject in need thereof, wherein the pharmaceutical composition comprises micro- and nano-$MgH_2$ compound particles and a pharmaceutically acceptable carrier and/or adjuvant and an effective concentration of $MgH_2$ is 60 mg/kg to 500 mg/kg wherein the micro- and nano-$MgH_2$ compound particles each have the particle diameter of 100 nm to 1,000 nm.

* * * * *